(12) United States Patent
Salminen et al.

(10) Patent No.: US 7,499,847 B2
(45) Date of Patent: Mar. 3, 2009

(54) CRYSTALLINE VAP-1 AND USES THEREOF

(75) Inventors: Tiina Salminen, Koski TI. (FI); Tomi Airenne, Turku (FI); Mark Johnson, Turku (FI); Heidi Kidron, Turku (FI); Yvonne Nymalm-Rejström, Turku (FI); Annu Söderholm, Espoo (FI); David Smith, Naantali (FI); Marjo Pihlavisto, Kaarina (FI); Lenita Viitanen, Turku (FI); Olli Pentikäinen, Lieto (FI); Tommi Nyrönen, Helsinki (FI)

(73) Assignee: Biotie Therapies Corporation, Turku (FI)

( * ) Notice: Subject to any disclaimer, the term of this patent is extended or adjusted under 35 U.S.C. 154(b) by 0 days.

(21) Appl. No.: 10/557,188

(22) PCT Filed: May 25, 2004

(86) PCT No.: PCT/FI2004/000318

§ 371 (c)(1),
(2), (4) Date: Nov. 17, 2005

(87) PCT Pub. No.: WO2004/104191

PCT Pub. Date: Dec. 2, 2004

(65) Prior Publication Data

US 2007/0093646 A1    Apr. 26, 2007

(30) Foreign Application Priority Data

May 26, 2003 (FI) .................................. 20030786
Feb. 20, 2004 (FI) .................................. 20040271

(51) Int. Cl.
G06G 7/58 (2006.01)
G06F 19/00 (2006.01)
G01N 31/00 (2006.01)
C07K 14/00 (2006.01)

(52) U.S. Cl. .............................. 703/11; 702/19; 436/4; 530/395

(58) Field of Classification Search ........................ None
See application file for complete search history.

(56) References Cited

U.S. PATENT DOCUMENTS 6,066,321 A    5/2000   Jalkanen et al.
2002/0173521 A1*  11/2002  Smith et al. .................. 514/315

FOREIGN PATENT DOCUMENTS

WO    WO-02/02090 A2    1/2002
WO    WO-03/006003 A1    1/2003
WO    WO-2005/080319 A1  9/2005

OTHER PUBLICATIONS

Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Pechkova et al. Protein nanocrystallography: a new approach to structural proteomics. Trends in Biotechnology. 2003. vol. 22, No. 3, pp. 117-122.*
Böhm et al., Journal of Computer-Aided Molecular Design, 1992, vol. 6, pp. 61-78.*
Goodsell et al., Journal of Molecular Recognition, 1996, vol. 9, pp. 1-5.*
RSCB Protein Databank webpages for 1US1 from Apr. 21, 2008—www.rcsb.org/pdb/explore/explore.do?structureId=1US1.*
RSCB Protein Databank webpages for 1PU4 from Apr. 21, 2008—www.rcsb.org/pdb/explore/explore.do?structureId=1PU4.*
Salmi, Marko et al., Immunity, vol. 14, Mar. 2001, pp. 265-276.
Shepard, Eric M. et al., Eur. J. Biochem., vol. 269, 2002, pp. 3645-3658.
Salminen et al., Protein Engineering, vol. 11, No. 12, 1998, pp. 1195-1204.
Izumi et al., Invest Ophthalmol Vis Sci 2002; 43:E-Abstract 1433, http://abstracts.iovs.org/cgi/content/abstract/32/12/1433?maxtoshow=& HITS=10&hit.
Nymalm et al., Acta Cryst, vol. D59, 2003, pp. 1288-1290.
Schuler et al., STN International, File ACS, STN Accession No. 1961:60877, Document No. 55:60877, Archives Internationales de Pharmacodynamie et de Therapie, 128, 431-68 (German) 1960.
Lehmann et al., STN International,. File CAPLUS, CAPLUS accession No. 1981:174504, document No. 94:174504, & Pharmazie, 35(5-6)m 278-84 (German) 1980.
D.J. Smith et al., "Cloning of Vascular Adhesion Protein 1 Reveals a Novel Multifunctional Adhesion Molecule", J. Exp. Med., vol. 188, No. 1, Jul. 6, 1998, pp. 17-27.
B. Cudney et al., Screening and Optimization Strategies for Macromolecular Crystal Growth, Acta Cryst, D50, 1994, pp. 414-423.
J. Jancarik et al., "Sparse matrix sampling: a screening method for crystallization of proteins", J. Appl. Cryst., vol. 24, 1991, pp. 409-411.
A. McPherson, "Crystallization of biological macromolecules", 1999, Cold Spring Harbor Laboratory Press, New York.

* cited by examiner

Primary Examiner—Suzanne M. Noakes
(74) Attorney, Agent, or Firm—Birch, Stewart, Kolasch & Birch, LLP.

(57) ABSTRACT

The present invention relates to crystalline vascular adhesion protein-1 (VAP-1) and in particular to methods for the use of structural information of crystalline human VAP-1 for ligand and/or inhibitor identification, design and production, as well as screening assays for detection of same. The invention further relates to inhibitors identified by the assays according to the present invention.

6 Claims, 4 Drawing Sheets

SEQUENCE LISTING

```
<160> NUMBER OF SEQ ID NOS: 5

<210> SEQ ID NO 1
<211> LENGTH: 2292
<212> TYPE: DNA
<213> ORGANISM: Homo sapiens

<400> SEQUENCE: 1
atgaaccaga agacaatcct cgtgctcctc attctggccg tcatcaccat ctttgccttg      60
gtttgtgtcc tgctggtggg caggggtgga gatgggggtg aacccagcca gcttccccat     120
tgcccctctg tatctcccag tgcccagcct tggacacacc ctggccagag ccagctgttt     180
gcagacctga gccgagagga gctgacggct gtgatgcgct ttctgaccca gcggctgggg     240
ccagggctgg tggatgcagc ccaggcccgg ccctcggaca actgtgtctt ctcagtggag     300
ttgcagctgc ctcccaaggc tgcagccctg gctcacttgg acaggggggag ccccccacct     360 gcccgggagg cactggccat cgtcttcttt ggcaggcaac cccagcccaa cgtgagtgag     420
ctggtggtgg ggccactgcc tcaccctcc tacatgcgcg acgtgactgt ggagcgtcat     480
ggaggccccc tgccctatca ccgacgcccc gtgctgttcc aagagtacct ggacatagac     540
cagatgatct tcaacagaga gctgccccag gcttctgggc ttctccacca ctgttgcttc     600
tacaagcacc ggggacggaa cctggtgaca atgaccacg ctccccgtgg tctgcaatca     660
ggggaccggg ccacctggtt tggcctctac tacaacatct cgggcgctgg gttcttcctg     720
caccacgtgg gcttggagct gctagtgaac cacaaggccc ttgaccctgc ccgctggact     780
atccagaagg tgttctatca aggccgctac tacgacagcc tggcccagct ggaggcccag     840
tttgaggccg gctggtgaa tgtggtgctg atcccagaca atggcacagg tgggtcctgg     900
tccctgaagt cccctgtgcc cccgggtcca gctccccctc tacagttcta tcccaaggc      960
```

```
cccccgcttca gtgtccaggg aagtcgagtg gcctcctcac tgtggacttt ctcctttggc   1020
ctcggagcat tcagtggccc aaggatcttt gacgttcgct tccaaggaga aagactagtt   1080
tatgagataa gcctccaaga ggccttggcc atctatggtg gaaattcccc agcagcaatg   1140
acgacccgct atgtggatgg aggctttggc atgggcaagt acaccacgcc cctgacccgt   1200
ggggtggact gccctactt ggccacctac gtggactggc acttcctttt ggagtcccag   1260
gcccccaaga caatacgtga tgccttttgt gtgtttgaac agaaccaggg cctcccccctg   1320
cggcgacacc actcagatct ctactcgcac tactttgggg gtcttgcgga acggtgctg   1380
gtcgtcagat ctatgtccac cttgctcaac tatgactatg tgtgggatac ggtcttccac   1440
cccagtgggg ccatagaaat acgattctat gccacgggct acatcagctc ggcattcctc   1500
tttggtgcta ctgggaagta cgggaaccaa gtgtcagagc acaccctggg cacggtccac   1560
acccacagcg cccacttcaa ggtggatctg gatgtagcag gactggagaa ctgggtctgg   1620
gccgaggata tggtctttgt ccccatggct gtgccctgga gccctgagca ccagctgcag   1680
aggctgcagg tgacccggaa gctgctggag atggaggagc aggccgcctt cctcgtggga   1740
agcgccaccc ctcgctacct gtacctggcc agcaaccaca gcaacaagtg gggtcacccc   1800
cggggctacc gcatccagat gctcagcttt gctggagagc cgctgcccca aaacagctcc   1860
atggcgagag gcttcagctg ggagaggtac cagctggctg tgacccagcg gaaggaggag   1920
gagcccagta gcagcagcgt tttcaatcag aatgacccct ggccccccac tgtggatttc   1980
agtgacttca tcaacaatga gaccattgct ggaaaggatt tggtggcctg ggtgacagct   2040
ggttttctgc atatcccaca tgcagaggac attcctaaca cagtgactgt ggggaacggc   2100
gtgggcttct tcctccgacc ctataacttc tttgacgaag accctccctt ctactctgcc   2160
gactccatct acttccgagg ggaccaggat gctggggcct gcgaggtcaa cccctagct   2220
tgcctgcccc aggctgctgc ctgtgccccc gacctccctg ccttctccca cgggggcttc   2280
tctcacaact ag                                                       2292
```

```
<210> SEQ ID NO 2
<211> LENGTH: 763
<212> TYPE: PRT
<213> ORGANISM: Homo sapiens

<400> SEQUENCE: 2

Met Asn Gln Lys Thr Ile Leu Val Leu Leu Ile Leu Ala Val Ile Thr
1               5                   10                  15

Ile Phe Ala Leu Val Cys Val Leu Leu Val Gly Arg Gly Gly Asp Gly
                20                  25                  30

Gly Glu Pro Ser Gln Leu Pro His Cys Pro Ser Val Ser Pro Ser Ala
        35                  40                  45

Gln Pro Trp Thr His Pro Gly Gln Ser Gln Leu Phe Ala Asp Leu Ser
    50                  55                  60

Arg Glu Glu Leu Thr Ala Val Met Arg Phe Leu Thr Gln Arg Leu Gly
65                  70                  75                  80

Pro Gly Leu Val Asp Ala Ala Gln Ala Arg Pro Ser Asp Asn Cys Val
                85                  90                  95

Phe Ser Val Glu Leu Gln Leu Pro Pro Lys Ala Ala Leu Ala His
                100                 105                 110

Leu Asp Arg Gly Ser Pro Pro Ala Arg Glu Ala Leu Ala Ile Val
            115                 120                 125

Phe Phe Gly Arg Gln Pro Gln Pro Asn Val Ser Glu Leu Val Val Gly
```

-continued

```
            130                 135                 140
Pro Leu Pro His Pro Ser Tyr Met Arg Asp Val Thr Val Glu Arg His
145                 150                 155                 160

Gly Gly Pro Leu Pro Tyr His Arg Arg Pro Val Leu Phe Gln Glu Tyr
                165                 170                 175

Leu Asp Ile Asp Gln Met Ile Phe Asn Arg Glu Leu Pro Gln Ala Ser
            180                 185                 190

Gly Leu His His Cys Cys Phe Tyr Lys His Arg Gly Arg Asn Leu
        195                 200                 205

Val Thr Met Thr Thr Ala Pro Arg Gly Leu Gln Ser Gly Asp Arg Ala
210                 215                 220

Thr Trp Phe Gly Leu Tyr Tyr Asn Ile Ser Gly Ala Gly Phe Phe Leu
225                 230                 235                 240

His His Val Gly Leu Glu Leu Val Asn His Lys Ala Leu Asp Pro
                245                 250                 255

Ala Arg Trp Thr Ile Gln Lys Val Phe Gln Gly Arg Tyr Tyr Asp
                260                 265                 270

Ser Leu Ala Gln Leu Glu Ala Gln Phe Glu Ala Gly Leu Val Asn Val
            275                 280                 285

Val Leu Ile Pro Asp Asn Gly Thr Gly Gly Ser Trp Ser Leu Lys Ser
        290                 295                 300

Pro Val Pro Pro Gly Pro Ala Pro Pro Leu Gln Phe Tyr Pro Gln Gly
305                 310                 315                 320

Pro Arg Phe Ser Val Gln Gly Ser Arg Val Ala Ser Ser Leu Trp Thr
                325                 330                 335

Phe Ser Phe Gly Leu Gly Ala Phe Ser Gly Pro Arg Ile Phe Asp Val
            340                 345                 350

Arg Phe Gln Gly Glu Arg Leu Val Tyr Glu Ile Ser Leu Gln Glu Ala
        355                 360                 365

Leu Ala Ile Tyr Gly Gly Asn Ser Pro Ala Ala Met Thr Thr Arg Tyr
    370                 375                 380

Val Asp Gly Gly Phe Gly Met Gly Lys Tyr Thr Thr Pro Leu Thr Arg
385                 390                 395                 400

Gly Val Asp Cys Pro Tyr Leu Ala Thr Tyr Val Asp Trp His Phe Leu
                405                 410                 415

Leu Glu Ser Gln Ala Pro Lys Thr Ile Arg Asp Ala Phe Cys Val Phe
            420                 425                 430

Glu Gln Asn Gln Gly Leu Pro Leu Arg Arg His His Ser Asp Leu Tyr
        435                 440                 445

Ser His Tyr Phe Gly Gly Leu Ala Glu Thr Val Leu Val Arg Ser
450                 455                 460

Met Ser Thr Leu Leu Asn Tyr Asp Tyr Val Trp Asp Thr Val Phe His
465                 470                 475                 480

Pro Ser Gly Ala Ile Glu Ile Arg Phe Tyr Ala Thr Gly Tyr Ile Ser
                485                 490                 495

Ser Ala Phe Leu Phe Gly Ala Thr Gly Lys Tyr Gly Asn Gln Val Ser
            500                 505                 510

Glu His Thr Leu Gly Thr Val His Thr His Ser Ala His Phe Lys Val
        515                 520                 525

Asp Leu Asp Val Ala Gly Leu Glu Asn Trp Val Trp Ala Glu Asp Met
    530                 535                 540

Val Phe Val Pro Met Ala Val Pro Trp Ser Pro Glu His Gln Leu Gln
545                 550                 555                 560
```

```
Arg Leu Gln Val Thr Arg Lys Leu Leu Glu Met Glu Glu Gln Ala Ala
                565                 570                 575

Phe Leu Val Gly Ser Ala Thr Pro Arg Tyr Leu Tyr Leu Ala Ser Asn
            580                 585                 590

His Ser Asn Lys Trp Gly His Pro Arg Gly Tyr Arg Ile Gln Met Leu
        595                 600                 605

Ser Phe Ala Gly Glu Pro Leu Pro Gln Asn Ser Ser Met Ala Arg Gly
    610                 615                 620

Phe Ser Trp Glu Arg Tyr Gln Leu Ala Val Thr Gln Arg Lys Glu Glu
625                 630                 635                 640

Glu Pro Ser Ser Ser Val Phe Asn Gln Asn Asp Pro Trp Ala Pro
                645                 650                 655

Thr Val Asp Phe Ser Asp Phe Ile Asn Asn Glu Thr Ile Ala Gly Lys
            660                 665                 670

Asp Leu Val Ala Trp Val Thr Ala Gly Phe Leu His Ile Pro His Ala
            675                 680                 685

Glu Asp Ile Pro Asn Thr Val Thr Val Gly Asn Gly Val Gly Phe Phe
        690                 695                 700

Leu Arg Pro Tyr Asn Phe Phe Asp Glu Asp Pro Ser Phe Tyr Ser Ala
705                 710                 715                 720

Asp Ser Ile Tyr Phe Arg Gly Asp Gln Asp Ala Gly Ala Cys Glu Val
                725                 730                 735

Asn Pro Leu Ala Cys Leu Pro Gln Ala Ala Cys Ala Pro Asp Leu
            740                 745                 750

Pro Ala Phe Ser His Gly Gly Phe Ser His Asn
        755                 760

<210> SEQ ID NO 3
<211> LENGTH: 115
<212> TYPE: PRT
<213> ORGANISM: Homo sapiens

<400> SEQUENCE: 3

Gly Gln Ser Gln Leu Phe Ala Asp Leu Ser Arg Glu Glu Leu Thr Ala
1               5                   10                  15

Val Met Arg Phe Leu Thr Gln Arg Leu Gly Pro Gly Leu Val Asp Ala
            20                  25                  30

Ala Gln Ala Arg Pro Ser Asp Asn Cys Val Phe Ser Val Glu Leu Gln
        35                  40                  45

Leu Pro Pro Lys Ala Ala Ala Leu Ala His Leu Asp Arg Gly Ser Pro
    50                  55                  60

Pro Pro Ala Arg Glu Ala Leu Ala Ile Val Phe Phe Gly Arg Gln Pro
65                  70                  75                  80

Gln Pro Asn Val Ser Glu Leu Val Val Gly Pro Leu Pro His Pro Ser
                85                  90                  95

Tyr Met Arg Asp Val Thr Val Glu Arg His Gly Gly Pro Leu Pro Tyr
            100                 105                 110

His Arg Arg
        115

<210> SEQ ID NO 4
<211> LENGTH: 131
<212> TYPE: PRT
<213> ORGANISM: Homo sapiens

<400> SEQUENCE: 4
```

```
Pro Val Leu Phe Gln Glu Tyr Leu Asp Ile Asp Gln Met Ile Phe Asn
1               5                   10                  15

Arg Glu Leu Pro Gln Ala Ser Gly Leu Leu His His Cys Cys Phe Tyr
            20                  25                  30

Lys His Arg Gly Arg Asn Leu Val Thr Met Thr Thr Ala Pro Arg Gly
                35                  40                  45

Leu Gln Ser Gly Asp Arg Ala Thr Trp Phe Gly Leu Tyr Tyr Asn Ile
        50                  55                  60

Ser Gly Ala Gly Phe Phe Leu His His Val Gly Leu Glu Leu Leu Val
65                  70                  75                  80

Asn His Lys Ala Leu Asp Pro Ala Arg Trp Thr Ile Gln Lys Val Phe
                85                  90                  95

Tyr Gln Gly Arg Tyr Tyr Asp Ser Leu Ala Gln Leu Glu Ala Gln Phe
            100                 105                 110

Glu Ala Gly Leu Val Asn Val Val Leu Ile Pro Asp Asn Gly Thr Gly
            115                 120                 125

Gly Ser Trp
    130
```

<210> SEQ ID NO 5
<211> LENGTH: 461
<212> TYPE: PRT
<213> ORGANISM: Homo sapiens

<400> SEQUENCE: 5

```
Ser Leu Lys Ser Pro Val Pro Pro Gly Pro Ala Pro Pro Leu Gln Phe
1               5                   10                  15

Tyr Pro Gln Gly Pro Arg Phe Ser Val Gln Gly Ser Arg Val Ala Ser
            20                  25                  30

Ser Leu Trp Thr Phe Ser Phe Gly Leu Gly Ala Phe Ser Gly Pro Arg
        35                  40                  45

Ile Phe Asp Val Arg Phe Gln Gly Glu Arg Leu Val Tyr Glu Ile Ser
        50                  55                  60

Leu Gln Glu Ala Leu Ala Ile Tyr Gly Gly Asn Ser Pro Ala Ala Met
65                  70                  75                  80

Thr Thr Arg Tyr Val Asp Gly Phe Gly Met Gly Lys Tyr Thr Thr
            85                  90                  95

Pro Leu Thr Arg Gly Val Asp Cys Pro Tyr Leu Ala Thr Tyr Val Asp
            100                 105                 110

Trp His Phe Leu Leu Glu Ser Gln Ala Pro Lys Thr Ile Arg Asp Ala
        115                 120                 125

Phe Cys Val Phe Glu Gln Asn Gln Gly Leu Pro Leu Arg Arg His His
    130                 135                 140

Ser Asp Leu Tyr Ser His Tyr Phe Gly Gly Leu Ala Glu Thr Val Leu
145                 150                 155                 160

Val Val Arg Ser Met Ser Thr Leu Leu Asn Tyr Asp Tyr Val Trp Asp
                165                 170                 175

Thr Val Phe His Pro Ser Gly Ala Ile Glu Ile Arg Phe Tyr Ala Thr
            180                 185                 190

Gly Tyr Ile Ser Ser Ala Phe Leu Phe Gly Ala Thr Gly Lys Tyr Gly
        195                 200                 205

Asn Gln Val Ser Glu His Thr Leu Gly Thr Val His Thr His Ser Ala
    210                 215                 220

His Phe Lys Val Asp Leu Asp Val Ala Gly Leu Glu Asn Trp Val Trp
```

-continued

```
            225                 230                 235                 240
Ala Glu Asp Met Val Phe Val Pro Met Ala Val Pro Trp Ser Pro Glu
                    245                 250                 255
His Gln Leu Gln Arg Leu Gln Val Thr Arg Lys Leu Leu Glu Met Glu
                260                 265                 270
Glu Gln Ala Ala Phe Leu Val Gly Ser Ala Thr Pro Arg Tyr Leu Tyr
            275                 280                 285
Leu Ala Ser Asn His Ser Asn Lys Trp Gly His Pro Arg Gly Tyr Arg
        290                 295                 300
Ile Gln Met Leu Ser Phe Ala Gly Glu Pro Leu Pro Gln Asn Ser Ser
305                 310                 315                 320
Met Ala Arg Gly Phe Ser Trp Glu Arg Tyr Gln Leu Ala Val Thr Gln
                325                 330                 335
Arg Lys Glu Glu Glu Pro Ser Ser Ser Ser Val Phe Asn Gln Asn Asp
                340                 345                 350
Pro Trp Ala Pro Thr Val Asp Phe Ser Asp Phe Ile Asn Asn Glu Thr
            355                 360                 365
Ile Ala Gly Lys Asp Leu Val Ala Trp Val Thr Ala Gly Phe Leu His
    370                 375                 380
Ile Pro His Ala Glu Asp Ile Pro Asn Thr Val Thr Val Gly Asn Gly
385                 390                 395                 400
Val Gly Phe Phe Leu Arg Pro Tyr Asn Phe Phe Asp Glu Asp Pro Ser
                405                 410                 415
Phe Tyr Ser Ala Asp Ser Ile Tyr Phe Arg Gly Asp Gln Asp Ala Gly
                420                 425                 430
Ala Cys Glu Val Asn Pro Leu Ala Cys Leu Pro Gln Ala Ala Ala Cys
            435                 440                 445
Ala Pro Asp Leu Pro Ala Phe Ser His Gly Gly Phe Ser
        450                 455                 460
```

CRYSTALLINE VAP-1 AND USES THEREOF

FIELD OF THE INVENTION

The present invention relates to crystalline human vascular adhesion protein-1 (VAP-1) and in particular to the use of structural information of crystalline human VAP-1 for ligand and/or inhibitor identification, design and production, as well as in silico and in vitro screening assays for detection of such ligands and/or inhibitors. The invention further relates to inhibitors identified by the assays according to the present invention, which are useful in the treatment of acute and chronic inflammatory conditions, diseases related to carbohydrate metabolism, aberrations in adipocyte or smooth muscle cell function and various vascular diseases.

BACKGROUND OF THE INVENTION

Physiological immune surveillance is dependent on the continuous patrolling of lymphocytes between the blood and different lymphoid organs. In normal non-lymphoid tissue lymphocytes are absent or only present at a very low level, but in many inflammatory disease states vast numbers of lymphocytes can accumulate in various affected tissues and organs. One of the important molecules controlling lymphocyte exit from the blood is vascular adhesion protein-1 (VAP-1) disclosed in U.S. Pat. No. 5,580,780. VAP-1 is a homodimeric 170-180 kDa endothelial glycoprotein. VAP-1 mediates lymphocyte binding to venules in human tissue sections. VAP-1 is heavily glycosylated and the sugar moieties are important for the adhesion function (Salmi et al., 1996). Blocking the adhesive function of VAP-1 reduces the number of cells infiltrating inflamed tissue allowing the inflammation to resolve. VAP-1 is thus a target for anti-inflammatory drug development.

Human vascular adhesion protein-1 (VAP-1) is a membrane-bound multifunctional glycoprotein with both adhesive and enzymatic properties. The cloning of VAP-1 surprisingly revealed that it belongs to the semicarbazide-sensitive monoamine oxidases (SSAO; EC 1.4.3.6) (International Patent Publication WO 98/53049). VAP-1 is a type 2 integral membrane protein with a large catalytically active extracellular domain. Thus VAP-1 is an ectoenzyme. Neither the role of SSAO activity nor its physiological substrates in leukocyte-endothelial interaction is well defined. VAP-1 was the first molecularly defined transmembrane member of this enzyme group in mammals, and it accounts for 90% of cellular SSAO activity. Notably, SSAOs are different from the well-characterized monoamine oxidases A and B in respect to subcellular localization, substrates, cofactors, inhibitors, and protein sequence.

Although the SSAO reaction has been known since the 1950's in biochemical terms, the physiological function(s) of these enzymes has remained enigmatic. The physiological substrates of SSAO are not known. Two potential candidates, methylamine and aminoacetone, are however formed during intermediary metabolism in humans and can be de-aminated by SSAO in vitro and in vivo.

VAP-1 SSAO activity has been proposed to be directly involved in the pathway of leukocyte adhesion to endothelial cells by a novel mechanism involving direct interaction with an amine substrate presented on a VAP-1 ligand expressed on the surface of a leukocyte (Salmi et al., 2001). This publication describes the direct involvement of VAP-1 SSAO activity in the process of adhesion of leukocytes to endothelium. Thus inhibitors of VAP-1 SSAO activity could be expected to reduce leukocyte adhesion in areas of inflammation and thereby reduce leukocyte trafficking into the inflamed region and therefore the inflammatory process itself.

In human clinical tissue samples expression of VAP-1 is induced at sites of inflammation. This increased level of VAP-1 can lead to increased production of $H_2O_2$ generated from the action of the VAP-1 SSAO extracellular domain on monoamines present in the blood. This generation of $H_2O_2$ in the localised environment of the endothelial cell could initiate other cellular events. $H_2O_2$ is a known signalling molecule that can upregulate other adhesion molecules and this increased adhesion molecule expression may lead to enhanced leukocyte trafficking into areas in which VAP-1 is expressed. Other products of the VAP-1 SSAO reaction may also have biological effects also contributing to the inflammatory process. Thus the products of the VAP-1 SSAO activity may be involved in an escalation of the inflammatory process, which could be blocked by specific SSAO inhibitors.

VAP-1 SSAO may be involved in a number of other pathological conditions associated with an increased level of circulating amine substrates of VAP-1 SSAO. The oxidative deamination of these substrates would lead to an increase in the level of toxic aldehydes and oxygen radicals in the local environment of the endothelial cell which could damage the cells leading to vascular damage. Increased levels of methylamine and aminoacetone have been reported in patients with Type I and Type II diabetes and it has been proposed that the vasculopathies such as retinopathy, neuropathy and nephropathy seen in late stage diabetes could be treated with specific inhibitors of SSAO activity.

The development of specific VAP-1 SSAO inhibitors that modulate VAP-1 activity would be useful for the treatment of acute and chronic inflammatory conditions or diseases such as chronic arthritis, inflammatory bowel diseases, and skin dermatoses, as well as diseases related to carbohydrate metabolism (including diabetes and complications resulting from diabetes, such as vasculopathies). In addition, aberrations in adipocyte dfferentiation or function and smooth muscle cell function (in particular, atherosclerosis), and various vascular diseases may be suitable for treatment with VAP-1 SSAO inhibitors.

International Patent Publication WO 03/006003 discloses carbocyclic hydrazino compounds as well as the use thereof as inhibitors of semicarbazide-sensitive amine oxidases (SSAO), including human Vascular Adhesion Protein-1 (VAP-1).

Copper-containing amine oxidases (CAOs; EC 1.4.3.6) belong to the functionally diverse superfamily of amine oxidases (Dawkes et al., 2001). They are also known as semicarbazide-sensitive amine oxidases since their enzymatic activity can be blocked by a carbonyl-reactive compound, semicarbazide. They catalyse the oxidative deamination of primary amines to the corresponding aldehydes in a copper-dependent reaction where molecular oxygen is consumed and hydrogen peroxide and ammonia are released. A characteristic feature for all CAOs is the use of 2,4,5-trihydroxyphenylalanine quinone, a topaquinone (TPQ), as a redox cofactor. CAOs have been isolated from several different organisms, including bacteria, fungi, plants and mammals. In plants CAOs are involved, e.g. in wound healing, whereas in prokaryotes CAOs allow the organism to utilize various amines metabolically as sources of nitrogen and carbon. In higher eukaryotes very little is known about the biological function of CAOs besides their role in the metabolism of biogenic and other amines.

Shepard et al., 2002, report striking differences in selectivity and rates of inactivation when testing inhibitors against six known copper-containing amine oxidases.

The crystal structures of CAOs have been solved from four different species: *Escherichia coli* (ECAO; e.g. Protein Data Bank, PDB code 1oac) (Parsons et al., 1995), *Pisum sativum* (PSAO; PDB code 1ksi) (Kumar et al., 1996), *Hansenula polymorpha* (HPAO; e.g. PDB code 1a2v) (Li et al., 1998) and *Arthobacter globiformis* (AGAO; e.g. PDB code 1av4) (Wilce et al., 1997). All of these homodimeric structures have a similar overall fold that can be divided into domains D1-D4 of which the D1 domain is found only in *E. coil*. Domains D2 and D3 are ~100 amino adds each and have an α/β type fold, whereas the largest, C-terminal domain D4 is ~400 amino adds in length and has a unique β-sandwich fold that is needed for dimerization. The active site, which is located in the D4 domain, is highly conserved within the CAO family. It is buried deeply within the protein and accessable only via a long channel surrounded mainly by amino acids from the D3 and D4 domains. The amino acid residues of the D3 domain are less conserved than the actual active site, suggesting that the cavity leading to the active site is of great importance in determining the substrate specificity of CAOs.

Even though the structures of known CAO proteins are quite similar, the sequence identity at the amino acid level is only 25-35%. The evolutionary relationship of VAP-1 to the structurally known members of the CAO family has not been characterized, but the presence of a transmembrane domain at the N-terminus of VAP-1 suggests substantial divergence from the soluble CAOs.

The present invention provides the crystallization and X-ray analysis of human VAP-1. This is the first mammalian CAO to be crystallized.

BRIEF DESCRIPTION OF THE INVENTION

The present invention relates to crystalline vascular adhesion protein-1 (VAP-1), especially human VAP-1.

The present invention provides means and methods for crystallizing purified VAP-1, analysing the obtained VAP-1 crystals, obtaining crystal parameters and X-ray diffraction data.

The present invention further relates to compositions comprising crystalline VAP-1 and the use of such compositions.

The present invention further provides structural information of crystalline human VAP-1, more specifically information on the active site cavity of human VAP-1, wherein said cavity is ~20 Å×~10 Å wide at the surface and ~15 Å deep and amino acids 86-87, 97, 168-173, 176-177, 180, 184, 205-212, 216, 227, 232-234, 236-239, 344, 388-390, 393-397, 415-419, 421, 421-426, 467-470, 647-651 and 758-761 from one monomer, and amino acids 443-449 and 451 of the other monomer of human VAP-1. More specifically said active site further comprises amino acid Leu469 at the top of a narrow ~4.5×~4.5 cavity at the bottom of the site, which is lined by amino acid residues Ala370, Tyr384, Asp386, Asn470, Tpq471 and Tyr473.

The present invention further provides a computer readable medium having stored thereon the atomic co-ordinate/X-ray diffraction data defining the three-dimensional structure of human VAP-1 protein, said medium being capable of displaying a three dimensional representation of a crystal of a molecule comprising a fragment of human VAP-1 protein when read by an appropriate machine and processed by a computer program for determining molecular structures.

The present invention further provides an in silico assay for de novo design of ligands and/or inhibitors comprising (i) identification of functional groups or small molecule fragments which can interact with sites in the active site of VAP-1, and (ii) linking these in a single compound.

The present invention further provides an in silico assay for screening known compounds and compound libraries for their ability of inhibiting VAP-1 activity.

The present invention further provides novel VAP-1 inhibitors useful for the treatment of acute and chronic inflammatory conditions or diseases such as chronic arthritis, inflammatory bowel diseases, and skin dermatoses, multiple sclerosis, as well as diseases related to carbohydrate metabolism (including diabetes and complications resulting from diabetes, such as vasculopathies). In addition, such inhibitors may be useful for treating aberrations in adipocyte differentiation or function and smooth muscle cell function (in particular, atherosclerosis), and various vascular diseases.

BRIEF DESCRIPTION OF THE DRAWINGS

In the following the invention will be described in greater detail by means of preferred embodiments and with reference to the attached figures, in which FIG. 1, Panel A shows a hexagonal VAP-1 crystal and Panel B a typical diffraction pattern.

DETAILED DESCRIPTION OF THE INVENTION

The present invention provides crystals of a mammalian copper-containing amine oxidase, CAO, especially crystals of human VAP-1.

To grow the crystals of the present invention a full-length protein, including the N-terminal transmembrane region, has to be purified to greater than 80% total protein and more preferably to greater than 90% total protein, most preferably to greater than 95% total protein. For expression and purification purposes the full length VAP-1 encoding sequence (SEQ ID NO. 1) is used. It is important that the purification method of choice is such that the purified protein retains its CAO activity, which may be determined using benzylamine as substrate.

A large number of vector-host systems known in the art may be used for recombinant production of the protein for the crystallization process. Possible vectors include, but are not limited to, plasmids or modified viruses, but the vector system must be compatible with the host cell used. As human VAP-1 is heavily glycosylated, eukaryotic hosts, such as yeast or animal cell hosts are preferred. Chinese Hamster Ovary (CHO) cells constitute most preferred host cells, these cells being fully capable of glycosylation.

Any crystallization technique known to those skilled in the art may be employed to obtain the crystals of the present invention, including, but not limited to, batch crystallization, vapour diffusion and micro dialysis. Standard micro and/or macro seeding of crystals may be used if required to obtain X-ray quality crystals.

The crystals of the present invention may form in the space group $P6_522$ with two molecules in the asymmetric unit and with unit dimensions of a=b=225.9 Å, c=218.7 Å, α=β=90°, γ=120° (see Example 2 below). However, the present invention contemplates crystals, which form in any space group including, but not limited to, $P6_522$. The crystals diffract to a resolution greater than 4 Å, preferably greater than 3 Å, most preferably greater than 2.8 Å.

To collect diffraction data from the crystals of the present invention, the crystals may be protected using cryoprotectants, such as glycerol, and flash-frozen in a nitrogen stream. The X-ray diffraction data may be processed with the XDS-program (Kabsch et al., 1993), but any method known to those skilled in the art may be used to process the X-ray diffraction data.

In order to determine the atomic structure of human VAP-1 according to the present invention, molecular replacement (MR), model building and refinement may be performed.

For determination of the VAP-1 structure molecular replacement may be employed using the known structures of the CAOs known in the art or any other CAO structure which may be determined as described above and below in Example 3.

Any method known to the skilled artisan may be employed to determine the three-dimensional structure of the protein of the present invention by molecular replacement. For example, the program AMORE of the CCP4i program suite may be employed to determine the structure of human VAP-1 using the atomic co-ordinates derived as described herein.

The atomic coordinates may be provided on a computer readable medium. Such a storage medium is preferable a random-access memory (RAM), a read-only memory (e.g. a CD-ROM) or diskette. The storage medium may be on a locally accessible computer, or remotely accessible through the internet.

An initial model of the three dimensional structure may be built using the program O (Jones et al., 1991) and refined using e.g., the REFMAC-program of the CCP4i program suite.

The refined three-dimensional VAP-1 structure according to the present invention is represented by the atomic coordinates and the structure determination statistics given in Table 1. The refined X-ray structure of VAP-1 dimer consists of residues A55-A761 with residues A1-A54, A202-A204 and A762-A763 not modelled in monomer A and of residues B57-B761 with residues B1-B56, B203, B742-B746 and B762-B763 not modelled in monomer B. Residues, A471 and B471 are topaquinones (Tpq471), which are formed by post-translational modification of an intrinsic tyrosine residue and are involved in the catalytic reaction. Both of the monomers contain one copper ion in the active site.

The information obtained from the three-dimensional structure of the present invention reveals that human VAP-1 active site (the substrate binding site) comprises (1) three histidines, His520, His522 and His684, coordinating the copper ion, (2) a catalytic base, Asp386, as well as (3) Tyr372 and Asn470, which is involved in positioning Tpq471, and (4) the active site gate residue, Tyr384. Tpq471 is in the 'on-copper' (inactive) conformation in the VAP-1 X-ray structure. Three-dimensional representations of the human VAP-1 structure are given in FIGS. 2 and 3.

Figure 2:
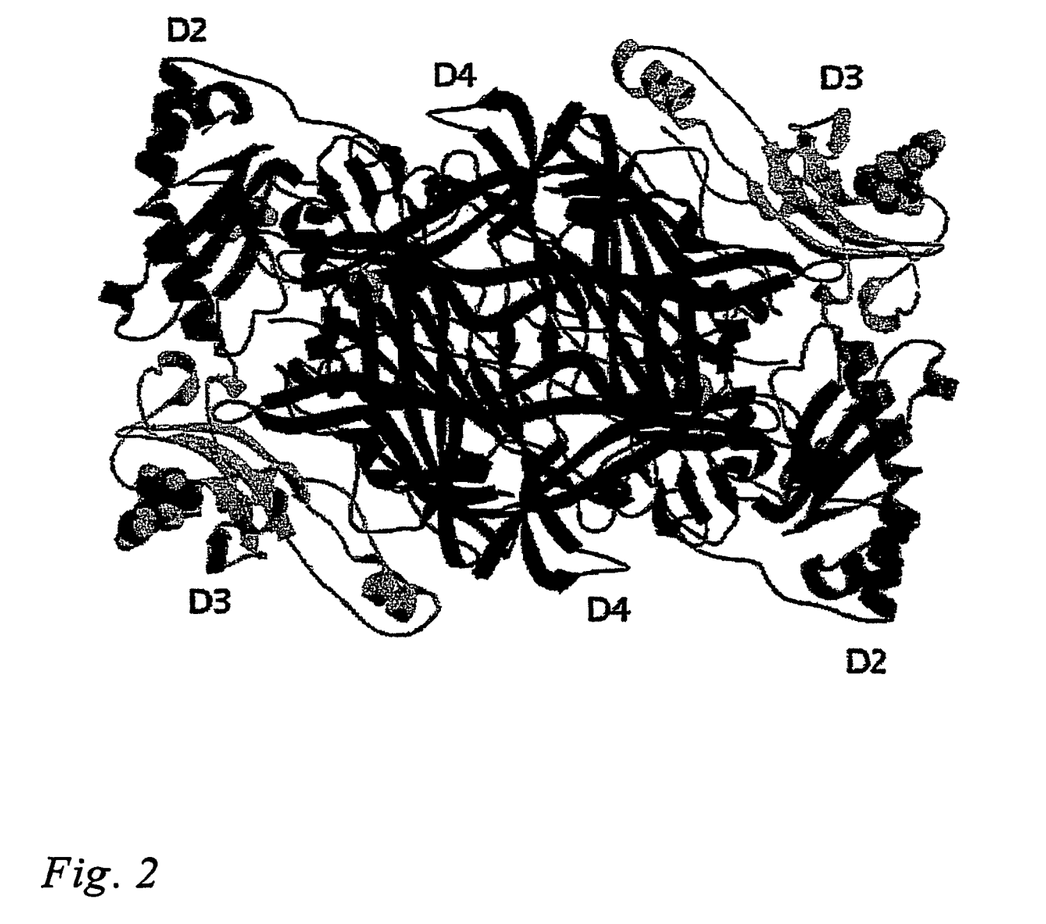
FIG. 2 shows the dimer of the human VAP-1 crystal structure, wherein the sugar units are drawn as space-filling models and the Tpg471 in both monomers is shown as a sphere in the D4-domain.
Figure 3:
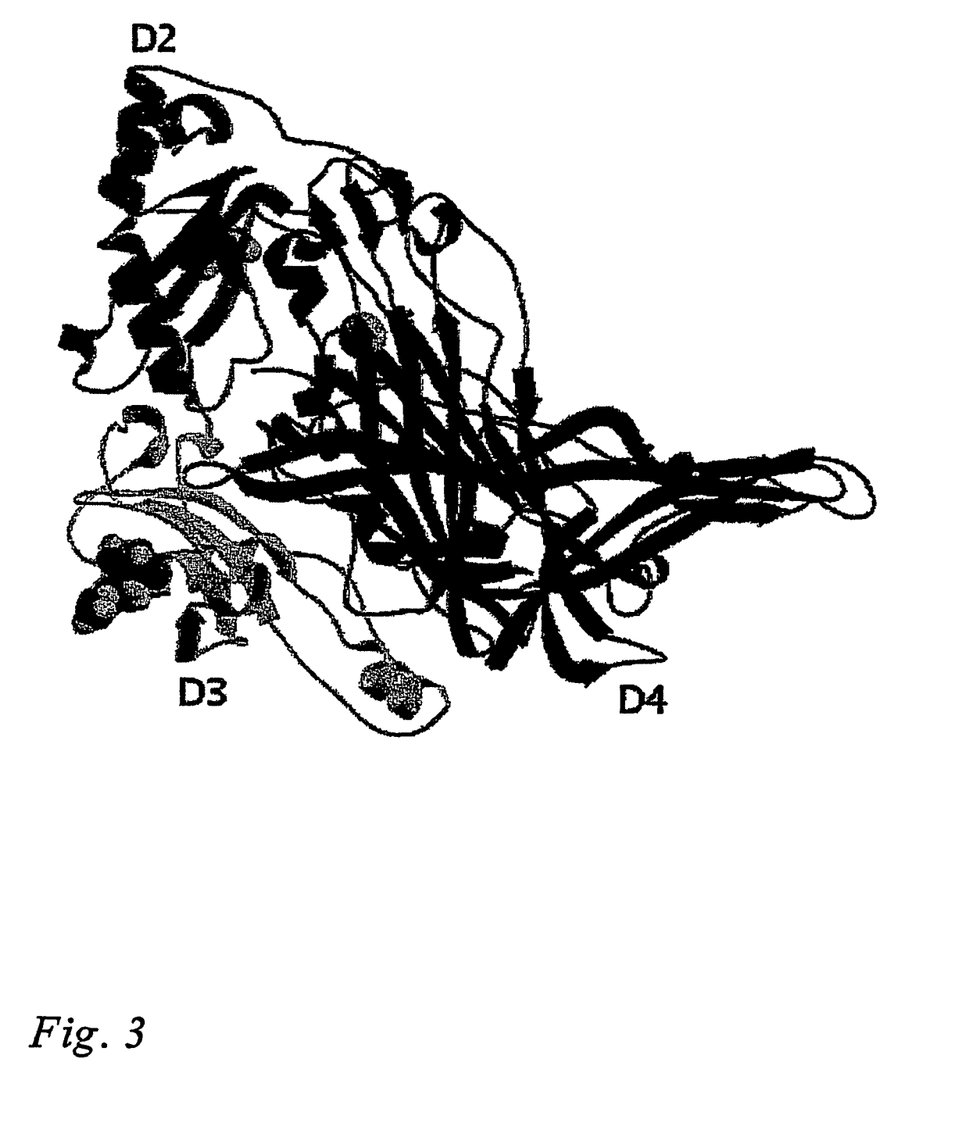
FIG. 3 shows one of the monomers of the dimeric VAP-1 crystal structure.

The VAP-1 active site is deeply buried and Tpq471 is located ~22 Å from the surface of the molecule. The active site cavity is ~20 Å×~10 Å wide at the surface and ~15 Å deep. At the bottom of the cavity Leu469, which is located on top of Tpq471, blocks the entrance to the active site in the VAP-1 X-ray structure. One wall of the cavity is composed of residues from the smaller D2 and D3 domains comprising e.g. 86-87, 97, 168-173, 176-177, 180, 184, 205-212, 216, 227, 232-234 and 236-239 and residues from the long β-hairpin arm protruding from the other monomer comprising 443-449 and 451. The other wall of the channel is composed of residues from the catalytic D4 domain comprising e.g. 344, 388-390, 393-397, 415-419, 421, 421-426, 467-470, 647-651, 758-761. At the entrance of the active site channel one sugar unit of the N-glycan attached to Asn232 is visible in the X-ray structure. Below Leu469 the ~7 Å long active site cavity is much narrower than at the surface and almost circular with dimensions of ~4.5×4.5 Å This part of the channel is lined by residues Ala370, Tyr384, Asp386, Asn470, Tpq471 and Tyr473.

VAP-1 X-ray structure surprisingly reveals an unique structure of the active site cavity. The cavity is extremely wide-mounted and open compared to the narrow active site channels in the ECAO, HPAO, PSAO and AGAO structures. Therefore, the active site cavity of VAP-1 can accommodate much larger ligand and inhibitor structures than the active site cavities of ECAO, HPAO, PSAO and AGAO. The residue corresponding to Leu469 in VAP-1 is glycine (ECAO, HPAO and AGAO) or alanine (PSAO) and, thus, it cannot block the active site in the ECAO, HPAO, PSAO and AGAO structures. Knowledge of this unique structure is necessary for designing a pharmacophore of human VAP-1 and specific ligand and inhbitor structures fitting the cavity.

This information can be used to define a pharmacophore of human VAP-1, i.e. a collection of chemical features and three-dimensional constraints expressing specific features necessary for biological activity. The pharmacophore preferably includes surface-accessible features, such as hydrogen bond donors and acceptors, charged groups or hydrophobic sites. Such features may be included in a pharmacophore model based on their relative importance to the biological activity.

Pharmacophores may be determined using available computer software, such as CATALYST, CERIUS or by using manual modelling based on known conformation of lead compounds. The pharmacophore may be used to screen in silico compound libraries, using available computer software, as described in more detail below.

In one embodiment of the invention the molecular modelling techniques are thus used for de novo compound design. De novo compound design refers to a process, where binding surfaces or active sites of target macromolecules, such as VAP-1, are determined and used as a basis for a rational design of compounds that interact with said binding surface or active site. The molecular modelling steps according to the present invention make use of the atomic coordinates of human VAP-1 and models of the active site. In a preferred embodiment the de novo drug design involves the identification of functional groups or small molecule fragments which can interact with the active sites in the binding surface of human VAP-1, and linking these groups or fragments into a single compound. Once functional groups or small molecule fragments which interact with the specific active site of human VAP-1 have been identified, these can be linked into a single compound using either bridging fragments having suitable size and geometry to fit the active site.

While linking of suitable functional groups and fragments may be performed manually, it is preferred to use suitable software, such as QUANTA or SYBYL. Further software known in the art are e.g., HOOK, which links multiple functional groups with molecular templates from a database, and CAVEAT, for designing linking units to constrained acyclic molecules. Other computer-based approaches for de novo compound design include LUDI, SPROUT and LEAP-FROG.

The present invention permits the use of molecular design techniques to design, identify and synthesize chemical entities and compounds, including inhibitory compounds, capable of binding to the active site of human VAP-1. The atomic coordinates of human VAP-1 may be used in conjunction with computer modelling using a docking program, such as e.g., GOLD, GRAM, DOCK, HOOK or AUTODOCK, to identify potential inhibitors of human VAP-1. This procedure can include computer fitting of potential inhibitors to the active site of VAP-1 to ascertain how well the shape and the chemical structure of the potential inhibitor will complement the active site. Examples of potential inhibitors designed by modelling with a docking program may conform to the general formula (I) as described below.

The present invention further includes an in silico method for identifying compounds that interact with the active site of human VAP-1, comprising the steps of (a) providing the atomic co-ordinates of the ligand binding domain of human VAP-1 in a storage medium on a computer, and (b) using the computer to apply molecular modelling techniques to the co-ordinates.

The above described structure model was further used for testing a library of molecules built and energy-minimized with Sybyl v.6.9 to assess their ability of acting as VAP-1 inhibitors. Prior to the in silico screening the VAP-1 X-ray structure was modified to mimic the 'off-copper' active conformation of CAOs as described in Example 4.

In a further embodiment of the present invention the in silico method is used for identifying compounds that specifically inhibit the enzymatic acitivity of human VAP-1, characterized by the following steps; providing a compound identified by said molecular modelling techniques, contacting said compound with human VAP-1 and detecting the interaction.

The three-dimensional structural information and the atomic coordinates associated with said structural information of VAP-1 is useful in rational drug design providing for a method of identifying inhibitory compounds which bind to and inhibit the enzymatic activity of VAP-1. Said method for identifying said potential inhibitor for an enzyme having SSAO-activity, comprises the steps of (a) using a three-dimensional structure of VAP-1 based on its atomic coordinates listed in Table 1; (b) employing said three-dimensional structure to design or select said potential inhibitor; (c) synthesizing said potential inhibitor; (d) contacting said potential inhibitor with said enzyme; and (e) determining the ability of said inhibitor to inhibit said SSAO activity.

The invention further encompasses compounds identified using the present in silico method for identifying compounds inhibiting the enzymatic activity of human VAP-1, or compounds that interacts with the active site of VAP-1.

Examples of potential VAP-1 inhibitors identifiable by the method of the present invention may be represented by formula (I)

wherein
$R^1$ is hydrogen, lower alkyl or an optionally substituted phenyl or heteroaryl group;
$R^2$ is hydrogen or lower alkyl, or
$R^1$ and $R^2$ may form together with the nitrogen atom to which they are attached a saturated heterocyclic ring;
$R^3$- $R^5$ represent each independently hydrogen, lower alky, aralkyl, optionally substituted phenyl or a heteroaryl group, or
$R^2$ and $R^3$ may form together with the atoms to which they are attached a saturated heterocyclic ring, or
$R^3$ and $R^5$ may form together with the carbon atoms to which they are attached a saturated carbocyclic ring;
$R^6$ is naphtyl, phenyl, substituted phenyl or a heteroaryl group;
$R^7$ is hydrogen, lower alkyl or aralkyl;
n is 1, 2 or 3; and
X=O, S, SO, $SO_2$ or $NR^2$.

Other types of compounds may equally well be identified using the methods and models according to the present invention. A man skilled in the art may, based on the atomic coordinates and the pharmacophore described herein, identify compounds that interact with the active site of the human VAP-1 protein. Generally, such potential inhibitor compounds may be characterized by a carbonyl group reactive agent, such as an amine or a hydrazine, as exemplified above, but other structures with a narrow protruding part fitting into the 4.5×4.5 Å bottom part of the active site cavity and capable of binding to the TPQ at the bottom of the active site are equally potential inhibitors. This protruding part of the compounds according to the present invention, is connected to a relatively hydrophobic middle part of about 7 Å length of the compound, acting both as a "linker", allowing the access of the protruding part to the active site, and interacting with amino acids Ala 370, Tyr384, Asp386, Asn470, Tpq471 and Tyr473 lining the cavity. Finally, the compounds according to the present invention comprise a bulkier part that fills the wide cavity and interacts with the exemplified amino acids 86-87, 97, 168-173, 176-177, 180, 184, 205-212, 216, 227, 232-234, 236-239, 344, 388-390, 393-397, 415-419, 421, 421-426, 467-470, 647-651, 758-761, 443-449 and 451 in the walls of the active site cavity.

Furthermore, the present invention provides assays and means for verifying the expected activity of the identified compounds.

The invention further encompasses the use of compounds identified by the present screening assays for the preparation of medicaments for the treatment of acute and chronic inflammatory conditions or diseases such as chronic arthritis, inflammatory bowel diseases, skin dermatoses and multiple sclerosis, as well as diseases related to carbohydrate metabolism (including diabetes and complications resulting from diabetes, e.g., vasculopathies, such as retinopathy, nephropathy and neuropathy). In addition, such inhibitors may be useful for treating aberrations in adipocyte differentiation or function and smooth muscle cell function (in particular, atherosclerosis), and various vascular diseases.

The invention further encompasses pharmaceutical compositions containing compounds identified by the present screening assays.

The following examples illustrate the present invention.

EXAMPLE 1

Production and Purification of Human VAP-1.

The full-length protein with the N-terminal transmembrane region was expressed in glycosylation-competent CHO cells, as described in Smith et al., 1998. The harvested cells were lysed using a lysis buffer (150 mM NaCl, 10 mM Tris-Base pH 7.2, 1.5 mM MgCl2, 1% NP40). Clarified cell lysate was used for the purification of HVAP-1 based on a monoclonal antibody affinity column and using the ÄKTA™ purifier system (Amersham Biotech). The protein was purified to homogeneity (>95%) using affinity chromatography and after purification the presence of the VAP-1 protein, the 90- and 170-180-kD bands, was confirmed by silver stained SDS-page as described by Smith et al. 1998.

The purified protein retained its CAO activity as determined using benzylamine as the substrate. Amine oxidase activity was measured using a spectrophotometric method as described (Hoft et al., 1997), 200 μl volume and 1 mM benzylamine as the substrate. The absorbance change was monitored in a Victor™ multi-label plate counter at 490 nm (PerkinElmer life Sciences).

The nucleotide sequence of the coding region of human VAP-1 is given in the sequence listing as SEQ ID NO. 1, and corresponding amino acid sequence (763 aa:s) as SEQ ID NO. 2.

EXAMPLE 2

Crystallization and Preliminary Analysis

Figure 1A:
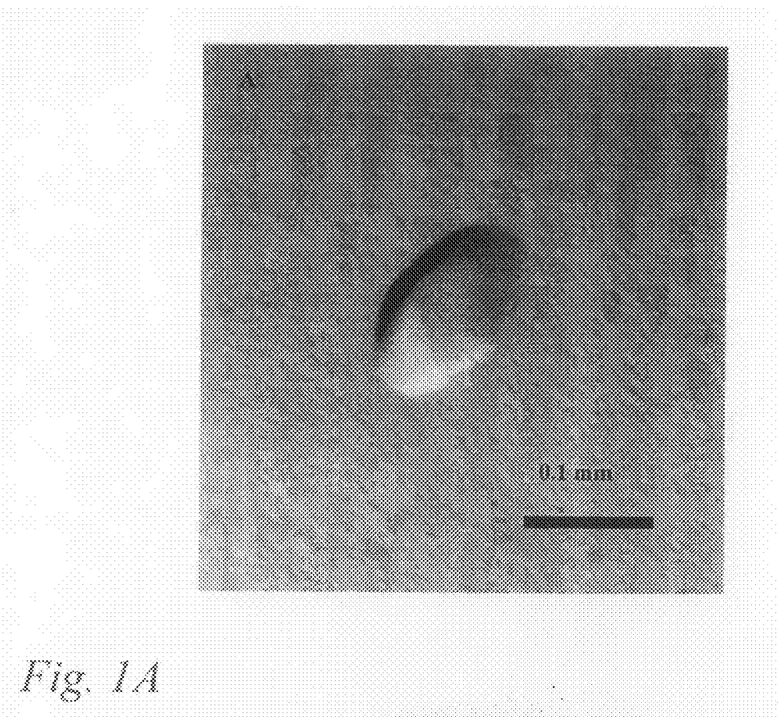
Figure 1B:
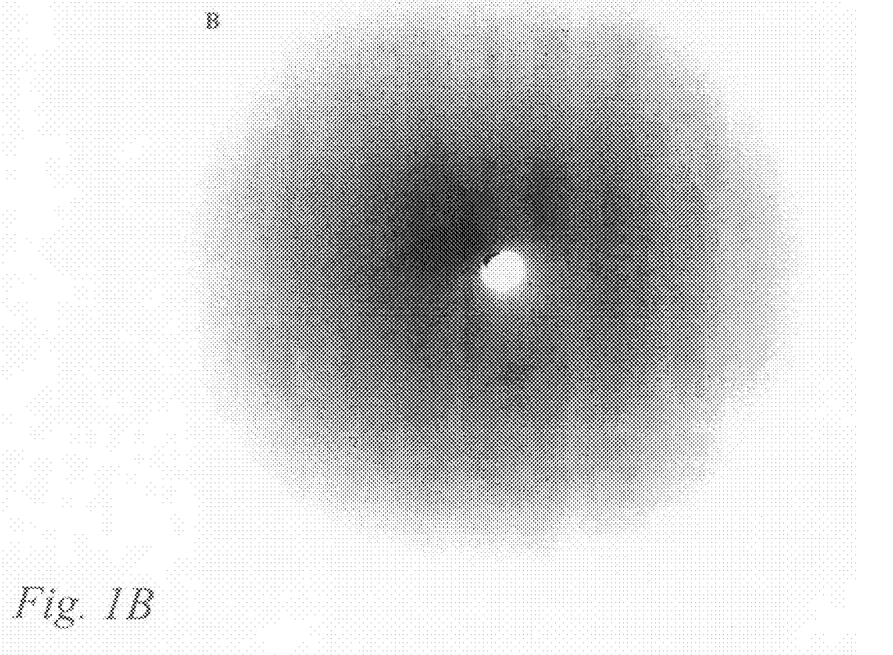

Initial crystallization conditions for hVAP-1 were screened at room temperature using the Wizard I random sparse matrix crystallization screen (Emerald BioStructures, Inc., USA) and the vapour-diffusion method. Small hexagonal crystals were obtained in a condition containing 1.0 M K/Na tartrate, 100 mM imidazole (pH 8.0) and 200 mM NaCl after several months of incubation. The hanging drops contained 2 µl of protein sample (1.0 mg/ml) in 10 mM potassium phosphate buffer (pH 7.2) and 2 µl of reservoir solution. After optimization the best crystals were obtained using a reservoir solution of 1.0 M K/Na tartrate, 100 mM imidazole .(pH 7.8) and 150-250 mM NaCl as the precipitant. The crystals formed in a few days and grew to a final size of about 0.15×0.15×0.1 mm (FIG. 1).

One crystal was mounted in a capillary and preliminary X-ray analysis was carried out in-house using a rotating-anode radiation source (Cu Kα radiation, 50 kV, 150 mA) and MAR345 image plate detector. The crystal, however, diffracted to only 8 Å resolution and the space group could not be accurately determined. All further X-ray analysis, as well as data collection, was carried out using synchrotron radiation at the beamline X11 (EMBL/DESY Hamburg, Germany) equipped with a MAR Research CCD detector. For data collection, the crystals were cryo-protected with 20% (v/v) glycerol and flash-frozen in a 100 K nitrogen stream. Diffraction data, collected from three different crystals, were processed with the program XDS. The solvent content and Matthews coefficient were calculated assuming a molecular weight of 90 kDa per monomer and using the CCP4 suite.

The best looking, hexagonal crystals were obtained using 1.0 M K/Na tartrate, 100 mM imidazole (pH 7.8) and 150-250 mM NaCl as the precipitant. The crystals grew to a typical size of 0.15×0.15×0.1 mm (FIG. 1a) with a unit cell dimension of a, b=225.9 Å, c=218.7 Å, α, β=90° and γ=120°. According to the diffraction data statistics (Table 1) the diffraction limit of the VAP-1 crystals was 3.2 Å, even though reflections corresponding to greater than 3.0 Å resolution were observed in some frames (FIG. 1b). The crystals belong to space group $P6_522$. Assuming the presence of one dimer (180 kDa) per asymmetric unit, the Matthews coefficient is 4.5 Å$^3$/Da and solvent content 72%. Crystal parameters and diffraction data statistics are summarized in Table 1.

TABLE 1

Crystal and diffraction data statistics.

| | |
|---|---|
| Space group | $p6_522^a$ |
| Unit cell lenghts (Å) | a = b = 225.9, c = 218.7 |
| Unit cell angles (°) | α, β = 90, γ = 120 |
| Matthews coefficient (Å$^3$Da$^{-1}$) | 4.5$^a$ |
| Solvent percentage | 72.3$^a$ |
| Unit cell volume (Å$^3$) | 9665176 |
| Molecules per asymmetric unit | 2$^a$ |
| Unique reflections | 52367 (4588) |
| Observed reflections | 739050 (61793) |
| Wavelength used (Å) | 0.811 |
| Resolution range (Å) | 20-3.20 (3.30-3.20) |
| Completeness (%) | 95.9 (97.2) |
| $R_{merge}$ (%) | 19.6 (46.4) |
| Average I/σ | 13.2 (6.0) |
| Redundancy | 14.1 (13.5) |

Values in parenthesis refer to the highest resolution shells.
$^a$See text for details.

EXAMPLE 3

Structure Determination

The structure of VAP-1 was solved by molecular replacement using the program AMORE (Navaza, 1994) of the CCP4i program suite (Collaborative Computational Project, 1994). This method confirmed that the space group of VAP-1 crystals was $P6_522$ with one biological unit, a dimer per asymmetric unit. Out of the dimeric polyalanine backbones of *Escherchia coli* CAO (residues 93-720; PDB code 1OAC), *Pisum sativum* CAO (residues 7-634; PDB code 1KSI), *Hansenula polymorpha* CAO (residues 22-655; PDB code 1A2V) and *Arthobacter globiformis* CAO (residues 9-623; PDB code 1AV4) tested in molecular replacement, the structure of *P. sativum* gave the best correlation coefficient (44.1%) and Rfactor (53.4%) and was used a search model.

Electron density maps were calculated with FFT of CCP4i suite and were predictable enough to trace the VAP-1 polypeptide, even though, at the beginning of building, in several fragments. The model was manually built using the program O and refined with REFMAC 5.1.24 (Murshudov et al., 1997) of the CCP4i suite to 3.2 Å resolution.

Side chains were step by step added to the structure between the numerous cycles of refinement. In the final model, only the following amino acids could not be traced and, thus, are not included in the structure. A1-A54, A202-A204, A762-A763, B1-B56, B203, B742-B746 and B762-B763. Coordinates for the topa-quinone residue were taken from Hetero-compound Information Centre, Uppsala (Kleywegt and Jones, 1998) and dictionary for it was generated with the program PRODRG (van Aalten et al., 1996). The stereo-chemical quality of the final VAP-1 model was assessed with PROCHECK (Laskowski et al., 1993)—out of the 1401 amino acids in the model, 84.0% occurred in the most favored regions in the Ramachandran plot (Ramachandran and Sasisekharan, 1968) and only 0.5% in the generously allowed or disallowed regions. A summary of the structure determination statistics is presented in Table 1. The atomic coordinates (and the structure factors) for the human VAP-1 crystal structure have been deposited in the PDB with the entry code 1PU4 and 1US1.

The crystalline form of human VAP-1 is a homodimer, each subunit containing the domains D2, D3 and D4. A schematic representation of the VAP-1 structure is shown in FIG. 2. The D2, D3 and D4 domains seen in the crystal structure, consist of residues ~55-169, 170-300 and 301-761, respectively (SEQ ID NO: 3, SEQ ID NO: 4 and SEQ ID NO: 5, respectively). The major differences in the structure of human VAP-1 compared to the other known structures of amine oxidases are seen in the domains D2 and D3, even though there are differences also in the domain D4.

EXAMPLE 4

In Silico Method for Screening Potential-Inhibitors

This example shows how a library of aryloxymethyl-substituted hydrazine alcohol compounds is screened in silico by docking into the binding cavity of VAP-1 described in Example 3. The compounds screened have the formula wherein
R[1] is hydrogen, lower alkyl or an optionally substituted phenyl or heteroaryl group;
R[2] is hydrogen or lower alkyl, or
R[1] and R[2] may form together with the nitrogen atom to which they are attached a saturated heterocyclic ring;
R[3]- R[5] represent each independently hydrogen, lower alkyl, aralkyl, optionally substituted phenyl or a heteroaryl group, or
R[2] and R[3] may form together with the atoms to which they are attached a saturated heterocyclic ring, or
R[3] and R[5] may form together with the carbon atoms to which they are attached a saturated carbocyclic ring;
R[6] is naphtyl, phenyl, substituted phenyl or a heteroaryl group;
R[7] is hydrogen, lower alkyl or aralkyl;
n is 1, 2 or 3; and
X=O, S, SO, $SO_2$ or $NR^2$.

Examples of compounds synthezised and/or built and screened in silico are given in Table 2:

TABLE 2

| Compound | Structure |
|---|---|
| 1 |  |
| 4 |  |
| 7 |  |

TABLE 2-continued

| Compound | Structure |
|---|---|
| 2 |  |
| 8 |  |
| 5 |  |
| 10 |  |
| 13 |  |
| 17 |  |

TABLE 2-continued

| Compound | Structure |
|---|---|
| 3 |  |
| 12 |  |
| 16 |  |
| 6 |  |
| 11 |  |
| 14 |  |
| 9 |  |
| 19 | |
| 20 | |

Modification of the X-ray Structure and Ligand Docking

The VAP-1 X-ray structure was modified to mimic the 'off-copper' active conformation of CAOs as described below. Firstly, topaquinone was modified to the active imino-quinone form according to the ECAO structure (PDB code 1D6Z (Wilmot et al., 1999)). Secondly, the active site cavity of the VAP-1 structure was modified prior to docking studies by choosing side chain rotamers (Phe389, Tyr394, Asp386 and Leu469) in the Bodil modeling package www.abo.fi/fak/mnf/bkf/research/johnson/bodil.html) that made the active site imino-quinone more accessible for the ligands. Hydrogen atoms were added to the VAP-1 structure used for screening and docking with the program Reduce v.2.15 without any side chain adjustment (Word et al., 1999).

R- and S-enantiomers of potential ligands were built and energy-minimized with Sybyl v.6.9 (Tripos Associates, St. Louis, USA). The ligands were covalently bound to the imino-quinone residue and manually docked into the binding cavity.

Ligand Binding Mode

Figure 4:
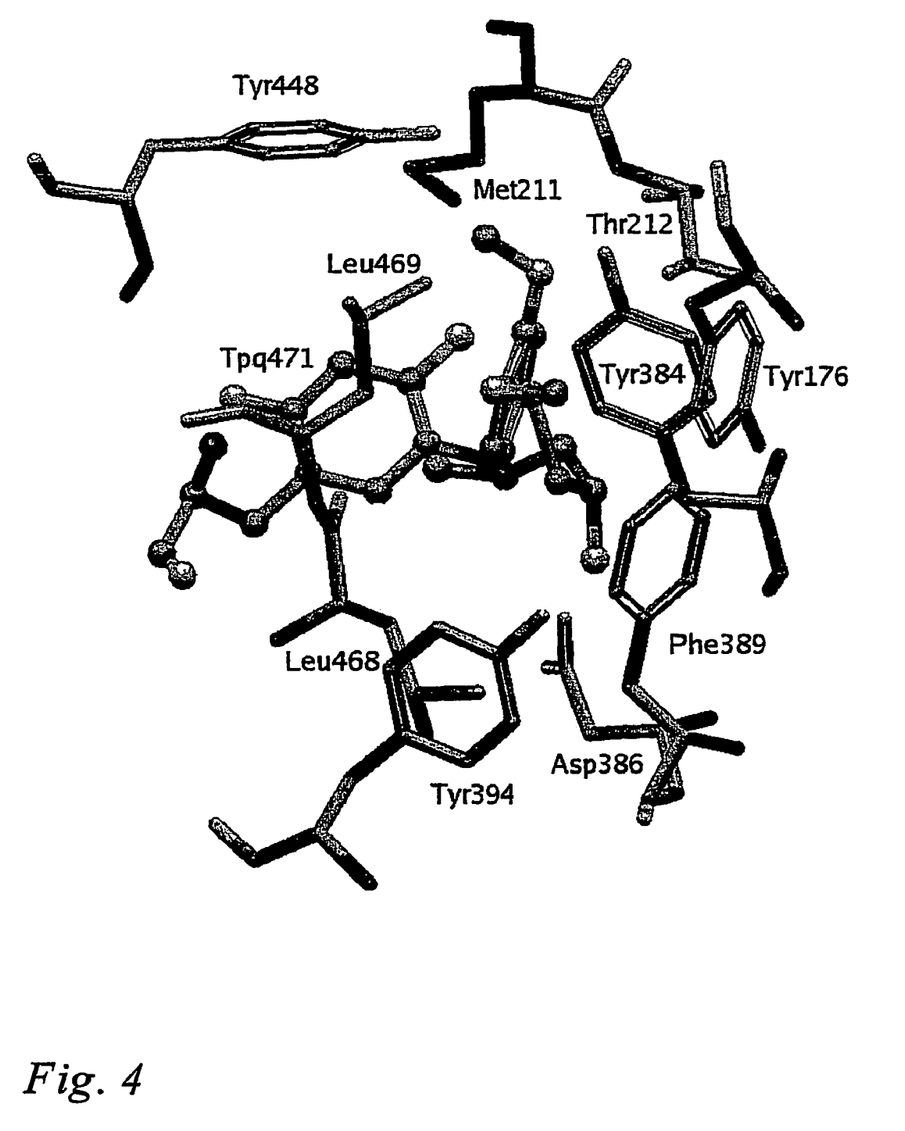
FIG. 4 shows the binding mode of a VAP-1 inhibitor compound in the VAP-1 structure. The point of view is down from the surface towards the active site.

FIG. 4 shows an example of the ligand screened. In FIG. 3, which is made using the Bodil modeling package, the binding mode of the S-enantiomer of BTT-2071 (Compound 9) is presented. The S-enantiomer of BTT-2071 was chosen to be an example ligand in the figure, since based on the docking simulations it is able to form the most extensive interactions with the VAP-1 structure.

Based on the VAP-1 structure, ligands where X is a sulphur atom instead of oxygen atom interact more favorably with VAP-1 since the interaction surface in VAP-1 is hydrophobic.

The hydrophobic part of the ligands including the sulphur atom packs against hydrophobic residues (Leu468, Leu469, Phe389 and Met211). The oxygen atom in the para-methoxyl group of the ligand is at the hydrogen bonding distance to the side chain oxygen of Thr212 whereas the oxygen atom in the meta-methoxyl group of the ligand is at the hydrogen bonding distance to the side chain hydroxyl group of Tyr394. Phe389 is located at a position where it can easily interact with the aromatic ring in the ligands. The methyl-groups in the para- and meta-methoxyl groups are in contact with Tyr448 and Tyr176, respectively. The hydroxyl group in the S-enantiomers can form an optimal hydrogen bond with Asp386 whereas in the R-enantiomers the hydrogen bonding distance and geometry are not optimal.

EXAMPLE 5

In Vitro Assay for Verifying VAP-1 Inhibitory Effect of the Identified Potential Inhibitors VAP-1 SSAO activity was measured using the coupled colourimetric method essentially as described for monoamine oxidase and related enzymes. Recombinant human VAP-1 SSAO expressed in Chinese Hamster Ovary (CHO) cells was used as a source of VAP-1 SSAO for activity measurements. Native CHO cells have negligible SSAO activity. These cells and their culture have previously been described (Smith D J et al., 1998).

A cell lysate was prepared by suspending approximately 3.6×10$^8$ cells in 25 ml lysis buffer (150 mM NaCl, 10 mM Tris-Base pH 7.2, 1.5 mM MgCl2, 1% NP40) and incubating at 4° C. overnight on a rotating table. The lysate was clarified by centrifugation at 18000 g for 5 min at room temperature and the supernatant used directly in the assay.

The VAP-1 SSAO assay was performed in 96 well microtitre plates as follows. To each well was added a predetermined amount of inhibitor if required. The amount of inhibitor varied in each assay but was generally at a final concentration of between 1 nM and 50 µM. Controls lacked inhibitor. The inhibitor was in a total volume of 20:1 in water. The following reagents were then added. 0.2M potassium phosphate buffer pH 7.6 to a total reaction volume of 200 µl, 45 µl of freshly made chromogenic solution containing 1 mM 2,4-dichlorophenol, 500 µM 4-aminoantipyrine and 4 U/ml horseradish peroxidase and an amount of CHO cell lysate containing VAP-1 SSAO that caused a change of 0.6 A490 per h. This was within the linear response range of the assay.

The plates were incubated for 30 min at 37° C. and the background absorbance measured at 490 nm using a Wallac Victor II multilabel counter. To initiate the enzyme reaction 20 µl 10 mM benzylamine (final concentration=1 mM) was added and the plate incubated for 1 h at 37° C.

The increase in absorbance, reflecting VAP-1 SSAO activity, was measured at 490 nm. Inhibition was presented as percent inhibition compared to control after correcting for background absorbance and IC50. values calculated using GraphPad Prism.

EXAMPLE 6

Comparison of VAP-1 SSAO Activity Versus Total Rat MAO Activity

Rat MAO was prepared from rat liver by rinsing a 1 g liver sample several times in 14 ml KCl-EDTA-solution to remove all blood. Then 1 g liver sample was homogenised in 4 ml ice-cold potassium phosphate buffer (0.1 M, pH 7.4) with an Ultra-Turrax homogeniser (setting 11 000 rpm, 4×10 s). After centrifugation at 500 g for 10 min at 4° C. the supernatant was carefully withdrawn and was centrifuged at 12 300 g for 15 min at 4° C. The supernatant was discharged and sedimented mitochondria were resuspended in 4 ml fresh phosphate buffer and centrifuged as previously. The mitochondria were suspended in 4 ml phosphate buffer and homogenized with an Ultra-Turrax homogeniser (setting 11 000 rpm, 2×10 s). Mitochondrial preparate was aliquoted and stored at −70° C.

Total MAO activity was measured in a similar way as for VAP-1 SSAO except that 2,4-dichlorophenol was replaced by 1 mM vanillic acid. To each well was added a predetermined amount of inhibitor if required. The amount of inhibitor varied in each assay but was generally at a final concentration of between 10 nM and 800 mM. Controls lacked inhibitor. The inhibitor was in a total volume of 20:1 in water. The following reagents were then added. 0.2 M potassium phosphate buffer pH 7.6 for a total reaction volume of 300 µl, 50 µl of freshly made chromogenic solution (as above) and 50 µl of MAO preparation.

The plates were incubated for 30 min at 37° C. and the background absorbance measured at 490 nm using a Wallac Victor II multilabel counter. To initiate the enzyme reaction 20 µl of 5 mM tyramine (final concentration 0.5 mM) was added and the plate incubated for 1 h at 37° C. The increase in absorbance, reflecting MAO activity, was measured at 490nm. Inhibition was presented as percent inhibition compared to control after correcting for background absorbance and IC50 values calculated using GraphPad Prism. Clorgyline and pargyline (inhibitors of MAO-A and -B respectively) at 0.5 µM were added to some wells as positive controls for MAO inhibition.

The ability of compounds of Table 3 to inhibit VAP-1 SSAO activity with specificity for VAP-1 SSAO over rat MAO is shown in Table 2. The results indicate that the compounds of the invention are specific inhibitors of human VAP-1 SSAO activity. The compounds of the present invention are therefore expected to have therapeutic utility in the treatment of diseases and conditions in which the SSAO activity of the human adhesion molecule VAP-1 plays a role.

TABLE 3

Potency and specificity of the compounds tested

| Compound | VAP-1 SSAO inhibitory activity IC$_{50}$ uM | Total MAO inhibitory activity IC$_{50}$ uM | Selectivity for VAP-1 SSAO over MAO |
|---|---|---|---|
| 1 (BTT-2066) | 0.37 | 13 | 35 |
| 4 | 0.43 | 10 | 23 |
| 7 | 0.44 | 6.0 | 14 |
| 10 | 0.55 | 6.0 | 11 |
| 13 | 0.64 | 3.3 | 5 |
| 16 | 0.35 | 7.4 | 21 |
| 2 | 0.52 | 8.7 | 17 |
| 5 | 0.52 | 4.0 | 8 |
| 8 | 0.65 | 10 | 15 |
| 11 (BTT-2067) | 0.27 | 11 | 41 |
| 14 | 0.37 | 3.4 | 9 |
| 17 | 0.43 | 6.1 | 14 |
| 3 | 0.26 | 3.3 | 13 |
| 6 | 0.09 | 3.3 | 37 |
| 9 (BTT-2071) | 0.21 | 41 | 195 |
| 12 (BTT-2072) | 0.33 | 37 | 112 |
| 15 (BTT-2072), S-enantiomer | 0.34 | 32 | 94 |
| 18 (BTT-2072), R-enantiomer | 0.39 | 21 | 62 |
| 19 (BTT 2073) | 0.20 | 8.8 | 45 |
| 20 | 0.34 | 9.6 | 28 |

It will be obvious to a person skilled in the art that, as the technology advances, the inventive concept can be implemented in various ways. The invention and its embodiments are not limited to the examples described above but may vary within the scope of the claims.

REFERENCES

Collaborative Computational Project, Number 4. (1994). *Acta Cryst*, D50, 760-763.

Dawkes, H. C. & Phillips, S. E. (2001). *Curr Opin Struct Biol*, 11, 666-673.

Holt, A., Sharman, D. F., Baker, G. B. & Palcic, M. M. (1997). *Anal Biochem*, 244, 384-392.

Kabsch, W. (1993). *Journal of Applied Crystallography*, 26, 795-800.

Kumar, V., Dooley, D. M., Freeman, H. C., Guss, J. M., Harvey, I., McGuirl, M. A., Wilce, M. C. & Zubak, V. M. (1996). *Structure*, 4, 943-955.

Li, R., Klinman, J. P. & Mathews, F. S. (1998). *Structure*, 6, 293-307.

Parsons, M. R., Convery, M. A., Wilmot, C. M., Yadav, K. D., Blakeley, V., Corner, A. S., Phillips, S. E., McPherson, M. J. & Knowles, P. F. (1995). *Structure*, 3, 1171-1184.

Salmi, M. & Jalkanen, S. (1996). *J Exp Med*, 183, 569-579.

Salmi, M. & Jalkanen, S. (2001). *Trends Immunol*, 22, 211-216.

Smith, D. J., Salmi, M., Bono, P., Hellman, J., Leu, T. & Jalkanen, S. (1998). *J Exp Med*, 188, 17-27.

Wilce, M. C., Dooley, D. M., Freeman, H. C., Guss, J. M., Matsunami, H., McIntire, W. S., Ruggiero, C. E., Tanizawa, K. & Yamaguchi, H. (1997). *Biochemistry*, 36, 16116-16133.

Jones, T. A., Zou, J. Y., Cowan, S. W., and Kjeldgaard (1991). Acta Crystallogr A 47 (Pt 2), 110-119.

Kleywegt, G. J., and Jones, T. A. (1998). Acta Cryst D 54, 1119-1131.

Laskowski, R. A, Macarthur, M. W., Moss, D. S., and Thomton, J. M. (1993). Journal of Applied Crystallography 26, 283-291.

Murshudov, G. N., Vagin, A. A, and Dodson, E. J. (1997). Acta Crystallogr D 53, 240-255.

Navaza, J. (1994). Amore—an Automated Package for Molecular Replacement. Acta Cryst A 50, 157-163.

Ramachandran, G. N., and Sasisekharan, V. (1968). Adv Protein Chem 23, 283-438.

Shepard, E. M., Smith, J., Bradley, O. E., Kuchar, J. A., Lawrence, M. S. and Dooley, D. M. (2002). Eurl J. Biochem. 269, 3645-3658.

van Aalten, D. M., Bywater, R., Findlay, J. B., Hendlich, M., Hooft, R. W., and Vriend, G. (1996). J Comput Aided Mol Des 10, 255-262.

Wilmot, C. M., Hajdu, J., McPherson, M. J., Knowles, P. F., and Phillips, S. E. (1999). Science 286(5445), 1724-8.

Word, J. M., Lovell, S. C., Richardson, J. S., and Richardson, D. C. (1999) J Mol Biol 285, 1735-47.

---

The invention claimed is:

1. A method for identifying a compound that interacts with human vascular adhesion protein 1 (VAP-1), comprising the steps of:
 a) providing a crystalline human vascular adhesion protein 1 (VAP-1), wherein VAP-1 comprises SEQ ID NO:2 and said crystal is defined as a crystal of space group P6$_5$22 with two molecules in the asymmetric unit and with unit dimensions of a=b=225.9 Å, c=218.7 Å, α=β=90°, γ=120°,
 b) determining the atomic coordinates for said human VAP-1 protein crystal of part a),
 c) providing the atomic co-ordinates from part b) on to a computer readable medium comprising a data storage material encoded with said atomic coordinates, wherein said data defines the active site cavity of dimeric human VAP-1 protein and said active site cavity is ~20 Å×~10 Å wide at the surface and ~15 Å deep and further comprises amino acid Leu469 at the top of a narrow ~4.5× ~4.5 cavity at the bottom of the site,
 d) using said computer and said atomic coordinates from c) to apply molecular modeling techniques to said coordinates,
 e) further providing atomic coordinates and the structure of a candidate compound, and
 f) identifying whether said compound interacts with human VAP-1 protein.

2. The method according to claim 1, wherein said molecular modeling techniques involve 'de novo' compound design.

3. The method according to claim 2, wherein said 'de novo' compound design involves: (i) identification of functional groups or small molecule fragments which can interact with sites in the active site of VAP-1, and (ii) linking these in a single compound.

4. The method according to claim 3, wherein the molecular modeling techniques use a pharmacophore of VAP-1.

5. The method according to claim 4, wherein the molecular modeling techniques use automated docking algorithms.

6. The method according to claim 4, further comprising:
 g) providing a compound identified by said molecular modeling techniques; and
 h) contacting said compound with human VAP-1 and detecting the inhibitory effect of said compound on the semicarbazide-sensitive monoamine oxidase (SSAO) activity of human VAP-1.

* * * * *